(12) United States Patent
Austin (10) Patent No.: US 8,696,747 B2
(45) Date of Patent: Apr. 15, 2014

(54) DEVICE FOR AN ORBITAL IMPLANT

(75) Inventor: Wayne Austin, Sheffield (GB)

(73) Assignee: Novamed Ceramisys Limited, Dundee (GB)

(*) Notice: Subject to any disclaimer, the term of this patent is extended or adjusted under 35 U.S.C. 154(b) by 1088 days.

(21) Appl. No.: 12/064,547

(22) PCT Filed: Aug. 25, 2006

(86) PCT No.: PCT/GB2006/050260
§ 371 (c)(1),
(2), (4) Date: Feb. 22, 2008

(87) PCT Pub. No.: WO2007/023319
PCT Pub. Date: Mar. 1, 2007

(65) Prior Publication Data
US 2008/0234816 A1    Sep. 25, 2008

(30) Foreign Application Priority Data
Aug. 25, 2005    (GB) .................................. 0517400.8

(51) Int. Cl.
*A61F 2/16*    (2006.01)
(52) U.S. Cl.
USPC .......................................... 623/6.64; 623/4.1
(58) Field of Classification Search
USPC ........................ 623/4.1, 5.11, 5.12, 5.13, 6.64
See application file for complete search history.

(56) References Cited

U.S. PATENT DOCUMENTS

| | | | |
|---|---|---|---|
| 5,466,258 A * | 11/1995 | Rubin | 623/6.64 |
| 6,187,041 B1 * | 2/2001 | Garonzik | 623/4.1 |
| 2004/0253279 A1 * | 12/2004 | Smith et al. | 424/400 |
| 2005/0125060 A1 * | 6/2005 | Perry et al. | 623/6.64 |
| 2005/0166384 A1 * | 8/2005 | Lenihan et al. | 29/433 |
| 2006/0069434 A1 * | 3/2006 | Durette | 623/6.64 |

FOREIGN PATENT DOCUMENTS

| | | |
|---|---|---|
| DE | 100 36 252 A1 | 2/2002 |
| FR | 2826281 A1 | 12/2002 |
| WO | WO 91/07930 A1 | 6/1991 |
| WO | WO 98/10715 A1 | 3/1998 |

OTHER PUBLICATIONS

Berghaus, Alexander et al.; "Porous Polyethylene and Proplast: There Behavior in a Bony Implant Bed"; Journal: European Archives of Oto-Rhino-Laryngology, Springer Berling, Jun. 2, 1984, pp. 115-123.*
Notification of Transmittal of the International Search Report and the Written Opinion of the International Search Authority, or the Declaration dated Nov. 30, 2006, for corresponding International Application No. PCT/GB2006/050260, 16 pgs.
International Preliminary Report on Patentability dated Mar. 6, 2008, for corresponding International Application No. PCT/GB2006/050260, 9 pgs.

* cited by examiner

*Primary Examiner* — David H Willse
*Assistant Examiner* — Tiffany Shipmon
(74) *Attorney, Agent, or Firm* — Shumaker & Sieffert, P.A.

(57) ABSTRACT

There is described a novel orbital implant having a smooth but macroporous outer surface, the said implant containing an integral resorbable platform for guided ocular muscle re-attachment.

27 Claims, 5 Drawing Sheets

Anterior

Posterior

Anterior

Posterior

DEVICE FOR AN ORBITAL IMPLANT

There is herein described a novel ceramic orbital implant having a smooth and porous outer surface, having fixed therein an integrated fixation platform for direct and guided ocular muscle re-attachment.

BACKGROUND

There are 6 ocular muscles responsible for normal eye movement. Historically when an eye removal (enucleation) was performed, the muscles were detached and not re-used. Glass, and then later silicone, spheres were used to fill the orbital void. These were simply placed into the orbit to replace the lost volume and did not transmit the movement generated from the disconnected ocular muscles, leading to an unnatural cosmetic effect. Furthermore, sagging of the lower eyelids occurred due to the high weight of the implants. The implants could later extrude, and could be uncomfortable.

In 1987 Perry A. C., (USA) described the use of a porous hydroxyapatite implant derived from natural coral as a substitute to the glass or silicone spheres. More recently in 1993, Porex Corp (USA) disclosed a similar porous product comprised of porous polyethylene. Several other products similar to the coral derivative now exist. FCI (CA) supply a porous implant of a similar nature comprised of synthetic alumina, and another called Molteno M-Sphere is derived from bovine cancellous bone. The porous nature of the device acts as a scaffold for the soft orbital tissue, including muscle tissue, that is in contact with the sphere and as such allows the tissue to grow entirely throughout the porous structure until it completely infiltrates all the pores creating a bicontinuous composite of porous implant and vascularised orbital tissue causing it to become a permanently integrated fixture. The ingrowth of the eye muscles anchors the muscles to the implant which then also transmits movement to the implant in conjunction with the remaining eye. However, there is in some cases the need for revision surgery to correct misalignment of eye movement using a peg system partly because the re-attachment points of the muscles are at the discretion of the operating surgeon.

In order to reattach the muscles they must be sutured in such a way so that they are in contact with the porous implant in the correct locations. Porous polyethylene, being a soft polymer, has the advantage that the muscles can be sutured directly to the implant. However the general opinion is that the biocompatibility of porous polyethylene is inferior to that of porous bioceramic implants, which are preferred by many surgeons in order to reduce complications to a minimum. Direct tissue apposition to the implant surface does not occur, instead a fibrous tissue layer first covers the implant.

Porous bioceramic implants are, like all ceramic materials, hard and naturally brittle and it is impossible, when attaching the muscles, to suture directly to the implant. When implanted, only the anterior-most portion is accessible and even if small tunnels could be created just through the anterior hemisphere through which suture needles could pass, it would be extremely difficult to carry this out during surgery and highly likely to damage the implant in the process. To overcome this problem, the surgeon can attempt to suture the muscles over and across the implant rather than directly to it, but the result is unreliable in terms of muscle reattachment and position. Alternatively, and far more commonly, a resorbable fabric mesh is wrapped entirely around the implant and secured at the posterior to create a tight mesh sac around the implant. The muscles can then be sutured directly to the fabric mesh.

The current technology however, presents a number of problems.

Figure 1:
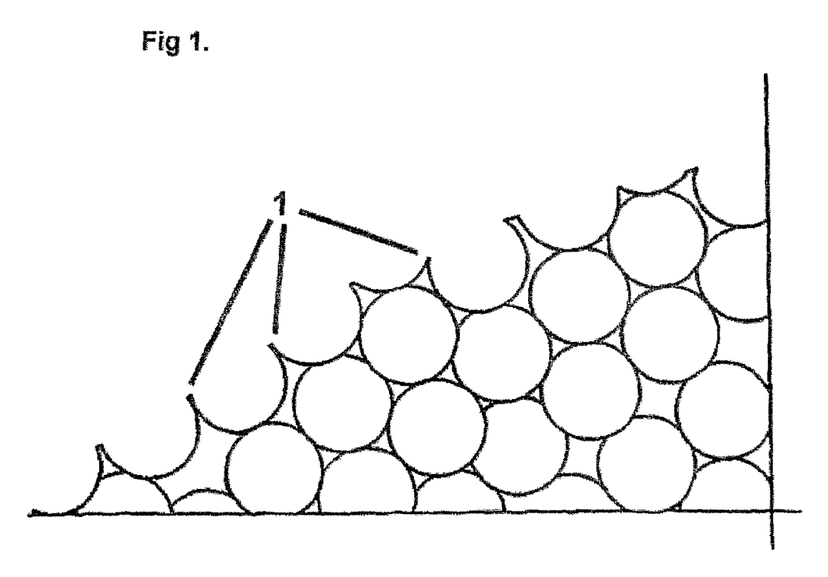
FIG. 1 shows an example of a typical rough surface of a standard machined ceramic orbital implant, illustrating the sharp spicules that drag on the orbital tissues.

The direct insertion of porous ceramic implants can be very problematic as the sharp spicules of the broken pores (See FIG. 1.(1)) at the rough surfaces of the implants exhibit a dragging effect on the orbital tissue, grabbing the tissues and inhibiting proper deep seating of the implant within the orbital cavity. Mesh wrapped implants do not alleviate this problem as the mesh itself is insufficiently smooth.

Additionally, the rough surfaces can increase the chance of exposure of the implant because of its rubbing on the wound closure.

Other wrapping materials have been used which are smooth such as sclera, bovine pericardium and temporalis fascia to which the muscles can also be sutured. These wrapping materials are smooth and do allow proper insertion with ease. However, windows and holes must be cut into the surfaces to allow the soft tissue and the ocular muscles access to the macroporous inner. Secondary, the use of donor sclera and bovine pericardium is now discouraged due to the possibility of infection and a self graft of temporalis fascia is an additional surgical step and site, and not used unless necessary.

A number of problems exist with porous orbital implant technology:
a) suturing the muscles directly to a ceramic implant surface
b) suturing the muscles in the correct location
c) the problem of creating a smooth ceramic surface to allow deep placement within the orbit and minimize implant exposure rates
d) the said smooth surface must immediately allow the unrestricted ingrowth of soft tissue in order to minimize healing time
e) the device construction materials must have excellent biocompatibility
f) the implant must be lightweight
g) the macropores in the body of the implant must have complete interconnectivity to avoid the possibility of infection The difficulties are interrelated, for example it would be of no practical use to create a smooth-surfaced implant unless the problem of suturing the muscles directly to the implant is first addressed, as a second material would still be required around the surface.

Although current devices have addressed some of these problems individually, there is a definite need for a spherical ceramic device which would address all of them. It would be advantageous for a device to provide a method of guided muscle re-attachment, eliminating both surgical error and the need to wrap the implant. If such a device could be provided, it would be more advantageous if the implant were to additionally have a smooth surface allowing the implant to be placed directly and easily, deep within the orbit, helping to prevent unwanted post-operative exposure. It would be of even greater benefit if the smooth surface were macroporous, allowing the maximum unrestricted ingrowth of vascular tissue without the need to have windows or holes cut through it. Finally it would be necessary for the implant body to be composed of a highly biocompatible bioceramic material and have a lightweight macroporous inner body that is completely interconnected and of a pore size suitable for the ingrowth and support of vascular tissue

PRIOR ART

It is well known to provide a spherical porous ceramic article for orbital implantation that allows cellular ingrowth of adjacent orbital tissues.

U.S. Pat. No. 4,976,731 and U.S. Pat. No. 6,063,117 both disclose orbital implant devices comprised of porous hydroxyapatite.

EP 0 746 270 is a modification of U.S. Pat. No. 4,976,731 and U.S. Pat. No. 6,063,117 and teaches the same orbital implant device having a polymeric or inorganic coating. However, in order to overcome the essential problem of allowing cellular ingrowth into the implant, holes and windows would need to be cut through the coating, and the disclosure does not teach how the muscles will be re-attached in the correct location.

US 2005/125060 is another modification of U.S. Pat. No. 6,063,117 or U.S. Pat. No. 4,976,731 where the coating is made up of two half shell cases which enclose the implant. The two half shells have different degradation rates. However, the smooth surface does require holes through to allow the tissues to contact the ceramic sphere. Whilst it teaches having some portions of the coating thinner in areas or fast resorbing, it still initially requires a complete coating. Holes and windows will typically need to be placed through the coating and it will still restrict the cellular ingrowth, particularly in the early days and weeks of the healing time.

U.S. Pat. No. 5,466,258 discloses a polymeric plug shaped orbital implant with a thin flange or lip through which a surgical needle can be passed and the positions for muscle re-attachment are defined. Polymeric devices can be sutured directly thereto, but biocompatibility is inferior to that of porous bioceramic implants EP 1 455 689 discloses a press manufactured, porous implant having a dense non-macroporous cap on the anterior surface. The cap addresses the problem of exposure of the implant due to rubbing on the wound closure, it also reports to have a smoother surface than typical implants, however the manufacturing route provides an irregular macroporous structure with irregular interconnections and there is no guarantee of complete interconnectivity, and it does not teach a method of direct muscle re attachment.

BRIEF SUMMARY OF THE INVENTION

According to a first aspect of the present invention, there is provided an orbital implant comprising a ceramic body including a plurality of through-holes adapted to receive biocompatible threads which, when threaded into the through-holes, provide a muscle attachment platform on an anterior side of the implant.

According to a second aspect of the present invention, there is provided an orbital implant comprising a ceramic body including a plurality of through-holes and at least one biocompatible thread threaded into the through-holes so as to provide a muscle attachment platform on an anterior side of the implant.

Preferably, the orbital implant is made of a ceramic material, for example aluminium oxide, hydroxylapatite or any other appropriate biocompatible material, for example an inorganic material.

The ceramic material is preferably porous or macroporous, with fully interconnected pores or macropores of diameter, for example, from 20 to 1000 μm, the pores or macropores defining an open scaffold throughout the structure.

Alternatively, the ceramic material has a smooth, non-macroporous surface, or at least non-macroporous surface regions.

The density of the implant may be from 0.2 to 0.9 g/cm³.

Additionally, cell walls of the device may have a microporosity (e.g. less than 50 μm) created by undersintering of ceramic particles to allow flow of nutrients and improve cellular ingrowth.

In currently preferred embodiments, there are provided four through-holes in a generally rectangular, preferably square, configuration. Alternatively, any other number of through-holes (though generally at least two) may be provided, generally arranged in a regular polyhedral configuration.

In addition to providing means for threading the biocompatible threads, the through-holes also help to allow more rapid soft tissue infiltration into the device after implant, reducing the healing time.

The through-holes or shafts may be in a direct, substantially parallel anterior to posterior alignment, or may be angled respectively inwardly, outwardly or a combination of the two.

The at least one biocompatible thread is preferably a resorbable thread that dissolves or is absorbed a predetermined time after implant of the device once it has served to act as a temporary muscle attachment platform.

The novel orbital implant described herein will thus allow direct and guided muscle re-attachment via the said platform (defined by the biocompatible threads) on its anterior hemisphere and optionally has a smooth exterior surface which will allow easy deep insertion into the orbital cavity, the said smooth surface also having open macropores communicating through the said surface allowing rapid tissue ingrowth without the need to modify or cut holes or windows therethrough. The implant does not require any coating material, and can be used in primary enucleation, secondary enucleation and evisceration procedures.

Uniquely the invention discloses a porous bioceramic orbital implant device to which the eye muscles can be sutured directly, eliminating the need for any coating or wrapping materials. Secondarily, the implant preferably has a smooth outer surface relative to the macroporous inner body which allows it to be placed deep into the orbital cavity without exerting a dragging effect on the orbital tissues, and will reduce the possibility of exposure from the device rubbing on the wound closure.

The device contains strategically placed shafts or through-holes passing through the implant, through and between which optionally resorbable strands may be passed creating a platform on the surface thereby allowing a method of direct and guided muscle re-attachment to a porous ceramic implant without the need for any wrapping or coating materials. The shafts additionally function to allow more rapid soft tissue infiltration to the centre of the implant, reducing the healing time. Additionally, the implant may have a smooth surface with open macropores communicating through said smooth surface allowing easy insertion into the orbital cavity and reducing exposure rates.

The main body of the implant may be composed of a bioceramic, highly macroporous fully interconnected foam type structure.

According to the invention in one aspect, there is provided a device for an orbital implant comprised of an interconnected highly macroporous, ceramic spherical body containing shafts through which resorbable strands are weaved to create a fixed platform for guided muscle re-attachment, the spherical body having a smooth, and macroporous outer surface.

The shafts are incorporated by machining or molding in a number of strategically placed narrow shafts running from the anterior hemisphere to the posterior hemisphere. The shafts can be in a direct anterior to posterior alignment or angled inwards or outwards. The number can range from between two and ten, but more preferably four to eight and even more preferably four. The arrangement of the shafts can be in any suitable pattern, but preferably in a square or angled ring (pentagon, hexagon etc) arrangement on the anterior hemisphere. The shafts may be placed equidistantly between 3 mm and 8 mm, but more preferably between 5 mm and 6 mm, back from the anterior-most point (the anterior pole) and may have a diameter between 0.5 and 3 mm.

It is one aspect of the current invention that four shafts are placed through the sphere parallel to the anterior-posterior alignment, and that they are arranged equidistantly from each other, with each shaft being 5 mm-6 mm back from the anterior pole forming the pattern of a square around the anterior pole.

Resorbable strands or threads can then be passed posteriorly to anteriorly, and vice versa, through and between the shafts with each pass being through one of the other shafts on that hemisphere preferably in a combination of clockwise and anticlockwise movements through and between adjacent shafts. The ends of the strands are secured at the posterior providing a platform of strands lying on the anterior surface between the shafts. This said platform provides guided muscle re-attachment points directly onto the ceramic surface. This process may be continued until more than one strand lies between the shafts. Preferably two or three strands will pass between adjacent shafts on the anterior hemisphere. The strands may be one single long strand passed many times or may be several separate strands forming one or several muscle re-attachment points each.

The strands may also form a pattern on the anterior hemisphere and knots holding the strands tightly may be visible on this hemisphere. In some embodiments of the invention such as providing the shafts in a square pattern mentioned herein, the pattern on the posterior pole may be repeated on the anterior pole and the implant may be used in either orientation.

The strands may be made from resorbable sutures well known to those skilled in the art of orbital surgery, or other biocompatible material, and the strands may be braided, twisted or knitted together to form multiple or intertwined strands. The strands could also be comprised of a material weaved together to form a thin mesh strip. It is preferable that the strands are resorbable over time and preferably between a period of 6 weeks and 2 years.

The position of the strands forming the muscle reattachment platform will be such that mimics the ideal placement of the ocular muscles. Typically, during primary and secondary implantation procedures, the four opposing rectus muscles are re-attached.

For each of these muscles the re-attachment position on the implant is typically, but not limited to, 5.5 mm away from the anterior pole.

It is another aspect of the invention that the muscle re-attachment platform comprises strands in a square pattern around the anterior pole with its corners 5 mm-6 mm away from the anterior-most point with the strands passing down through four shafts in the implant through to the posterior at each corner, and between each adjacent shaft thus forming the sides of a square pattern.

The smooth surface, where provided, is an integral part of the monolithic ceramic device and is a direct result of forming the macroporous ceramic sphere. The surface need not be a coating or application of a substance. The entire surface of the implant may be smooth relative to the macroporous ceramic body within, and the surface finish on the implant mirrors that of a mold into which the macroporous foam may be placed during the forming stage of the manufacturing process. Thus, if the concave interior of the mold has a smooth finish, then the implant will have an identical smooth surface.

Chemical agents can be added to the mold inner surface which when used, during the forming stage to create an implant, can act on the surface macropores of the implant that the said agents contact. This can in turn affect the number of open macropores, and their sizes, on the surface of the implant. The surface of the mold can itself be made of a substance which imparts the desired affect on the surface macropores during the forming stage. A person skilled in the art will be well aware of the properties of different molding materials.

It is another aspect of the invention that the entire smooth surface is porous and contains a multitude of open macropores communicating to the exterior through the surface, between 20 and 1000 microns but more preferably 50-200 microns, the said macropores also communicating directly with the interconnected macroporous body within, through which the vascular tissue and muscles can grow and directly access the body of the implant.

It is another aspect of the invention that the manufacturing process can be controlled or the surface machined away so that the smooth surface does not cover between 10% and 40% of the implant forward from the posterior most point (posterior pole).

It is also another aspect of the invention that the manufacturing process can be controlled or the smooth surface machined away so that small windows or areas, around and under where the strands forming the muscle re-attachment platform lie, are created through the smooth surface. Thus the muscles, when reattached, can directly contact the macroporous interior.

It is another aspect of the invention that the entire surface can be smooth and non-macroporous and the manufacturing process can be controlled or the surface machined away so that small windows or areas, around and under where the strands forming the muscle re-attachment platform lie, are created through the smooth surface, and that the said smooth surface does not cover between 10% and 40% of the implant forward from the posterior pole.

The ceramic device is preferably comprised of aluminium oxide or hydroxylapatite, although it could be made of any other biocompatible inorganic material.

It is an aspect of the invention that the macropores of the inner body of the implant are fully interconnected providing an open scaffold throughout the implant with predominantly each macropore being between 50 and 1000 um in size, and the density of the implant being between 0.2 grams per cubic centimeter and 0.9 grams per cubic centimeter, such as, e.g., between 0.2 grams per cubic centimeter and 0.8 grams per cubic centimeter. Additionally, the macroporous cell walls of the device may contain microporosity (<50 microns) created by undersintering of the ceramic particles to allow the flow of nutrients and maximise the cellular ingrowth.

It is an object of embodiments of the current invention to mitigate all the above said problems of orbital implants rather than addressing just one or two of them, by disclosing a low mass, highly macroporous ceramic orbital implant characterised in that it comprises biocompatible strands passed a multiplicity of times through and between shafts through the body of the implant, creating a muscle re-attachment platform on the anterior hemisphere for muscle fixation.

BRIEF DESCRIPTION OF THE DRAWINGS

For a better understanding of the present invention and to show how it may be carried into effect, reference shall now be made by way of example to the accompanying drawings, in which.

In the present drawings, the macropores depicted in FIGS. 1 and 2 are all identical. In practice, the macropores will have a range of different pore sizes, however this does not detract from the object of the illustrations, and the actual pore sizes and ranges of an embodiment of the invention are illustrated in the micrograph of FIG. 5.

DETAILED DESCRIPTION OF THE DRAWINGS

FIG. 1 shows, in schematic form, a cross-section through an edge of a prior art ceramic, porous orbital implant. It can be seen that the surface is not smooth, but has sharp spicules 1 that can drag on and damage orbital tissues.

Figure 2:
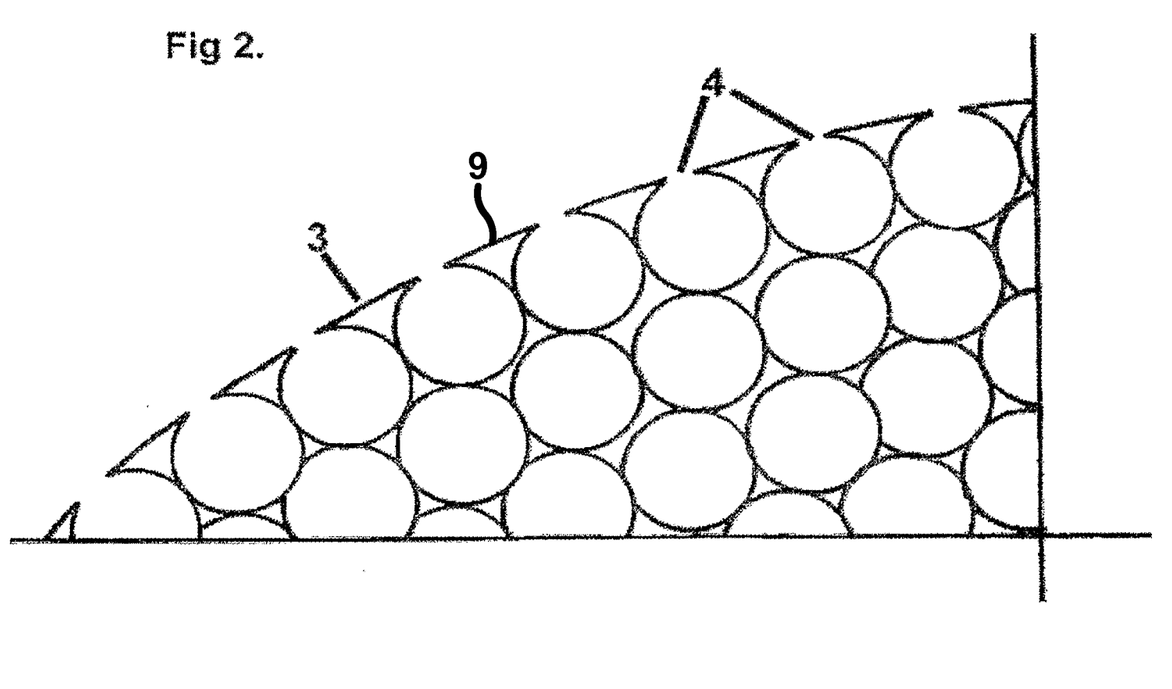
FIG. 2 illustrates the smooth surface produced by embodiments of the invention herein in contrast to FIG. 1, and illustrates outer pores interconnecting through the surface producing a smooth but porous outer surface.

FIG. 2 shows, in schematic form, a cross-section through an edge of a ceramic, macroporous orbital implant of an embodiment of the present invention, which comprises a relatively smooth outer surface 3 with outer pores 4 interconnecting through the surface 3 producing a smooth but porous outer surface. The orbital implant includes non-porous portions 9 which are separated by outer pores 4.

Figure 3:
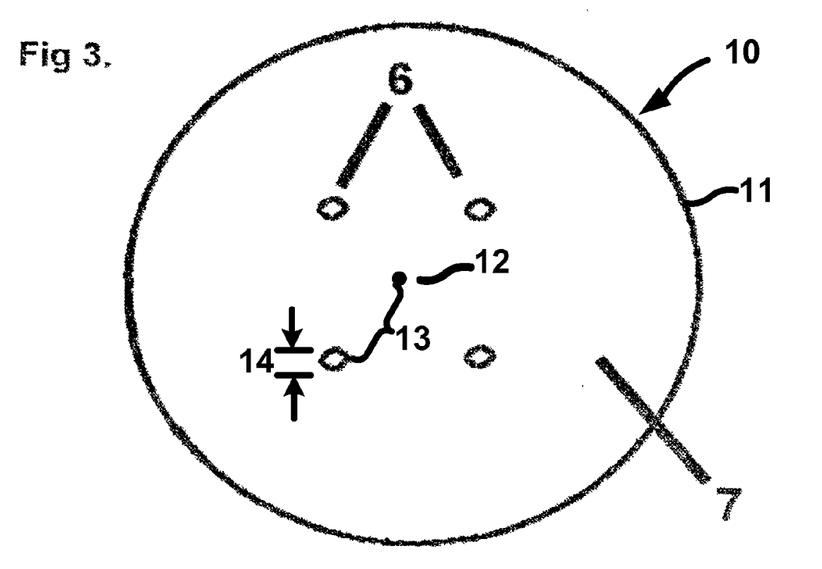
FIG. 3 illustrates an example plan view of an anterior hemisphere showing four shafts which run directly through the implant to a posterior pole.

FIG. 3 shows a currently preferred embodiment of the invention comprising four through-holes or shafts 6 provided in an anterior hemisphere 7 of orbital implant 10. Orbital implant 10 includes portions of an outer surface 11 that are non-porous. In the example of FIG. 3, through-holes or shafts 6 are arranged relative to an anterior point 12 of orbital implant 10 and are shown as substantially equidistance from each other. In some examples, through-holes or shafts 6 are located from anterior point 12 by a distance 13, which in some examples may be from 2 mm to 10 mm, such as, e.g., from 3 mm to 7 mm, or from 4 mm to 6 mm. Through-holes or shafts 6 define a diameter 14, which in some examples may be from 0.5 mm to 3 mm.

Figure 4:
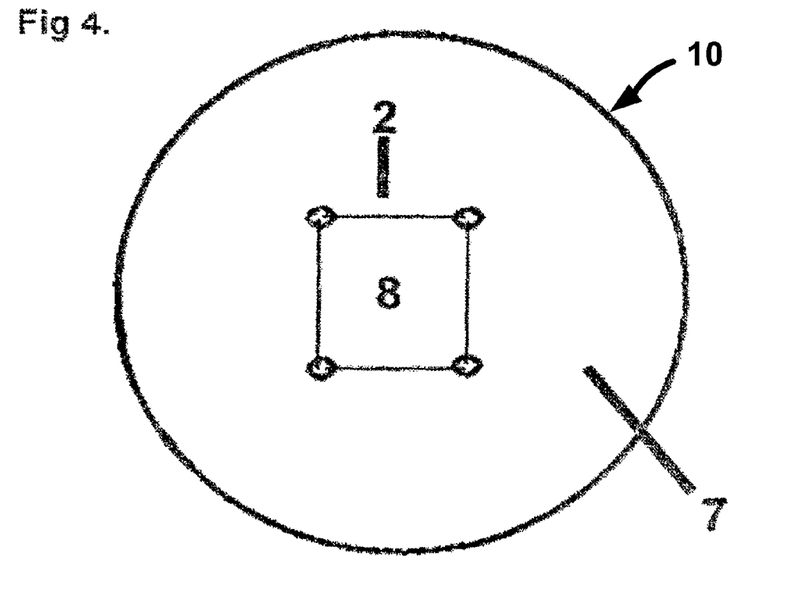
FIG. 4 illustrates an example plan view of the anterior hemisphere showing strands crossing between and down through the shafts creating a square muscle re-attachment platform on the anterior hemisphere around the anterior pole.

FIG. 4 shows the embodiment of orbital implant 10 of FIG. 3 further provided with biocompatible threads or strands 2 threaded in a square pattern 8 through the shafts 6 so as to provide a muscle re-attachment platform 8.

Figure 5:
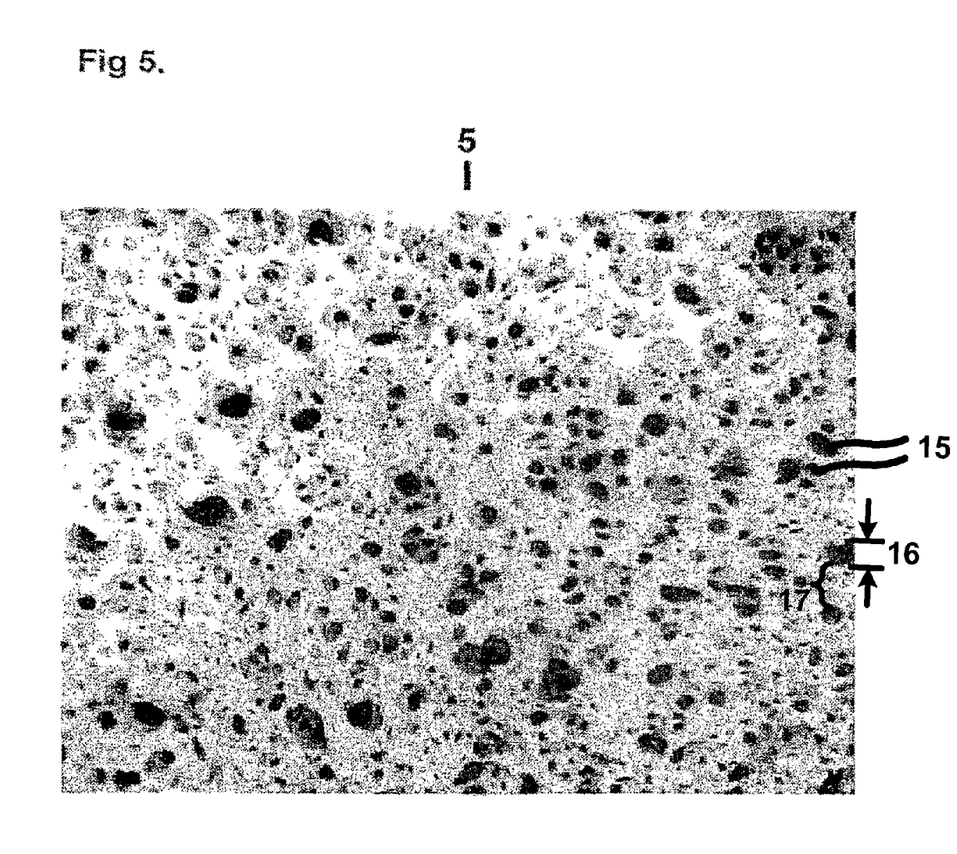
FIG. 5 provides a pictorial representation of an example cross sectional view of a small portion of the highly macroporous, and fully interconnected interior body of an implant of an embodiment of the present invention.

FIG. 5 is a micrograph showing the actual macroporous structure 5 of an implant of the present invention. In FIG. 5, pores 15 are fully interconnected to define an open scaffold throughout the structure 5, e.g., for ingrowth and support of vascular tissue. In some examples, pores 15 define a diameter 16. Diameter 16 may be from 20 to 1000 μm, although the disclosure is not limited in this respect. In some examples, different pores of pores 15 are spaced from each other by a distance 17. In some examples, distance 17 ranges from 50 to 1000 μm such as, e.g., from 200 to 800 μm.

Figure 6A:
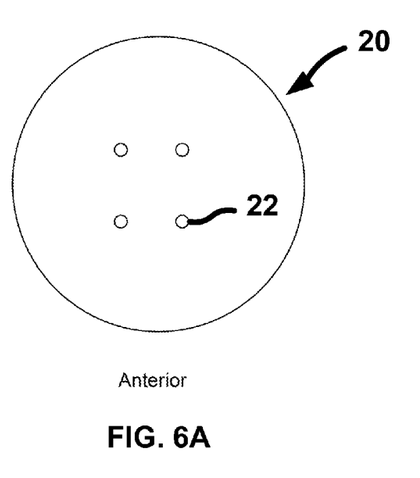
Figure 6B:
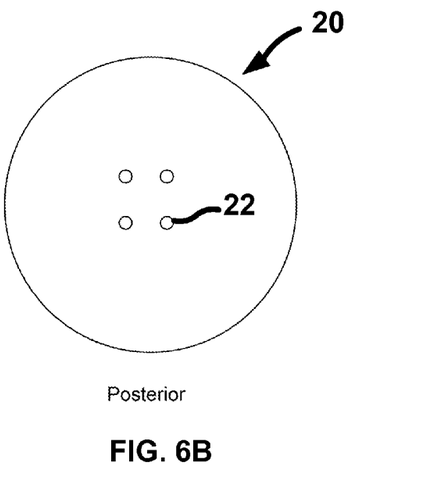

FIGS. 6A and 6B show example plan views of an anterior hemisphere and a posterior hemisphere, respectively, of an example orbital implant 20. Orbital implant 20 includes a plurality of through-holes 22, which in the example of FIGS. 6A and 6B are shown as four through-holes 22. Through-holes 22 converge from an anterior direction to a posterior direction as the through-holes 22 pass through orbital implant 20.

Figure 7A:
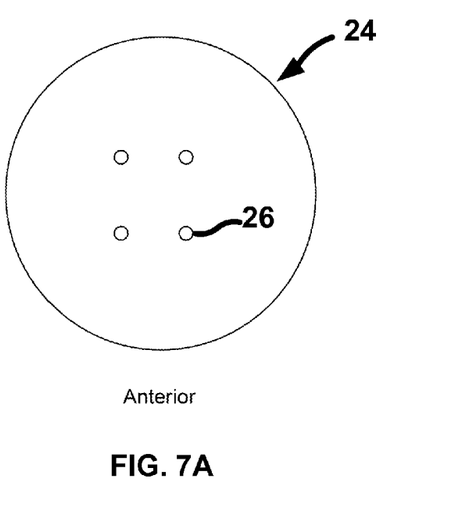
Figure 7B:
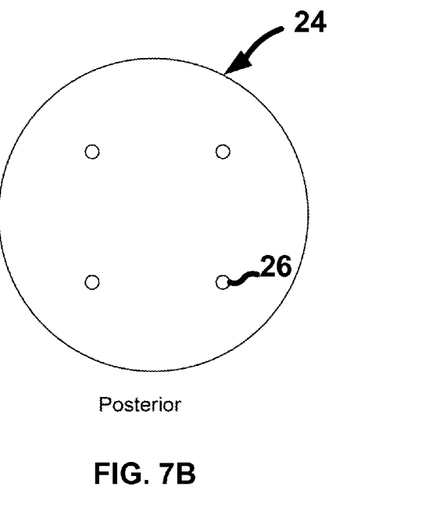

FIGS. 7A and 6B show example plan views of an anterior hemisphere and a posterior hemisphere, respectively, of an example orbital implant 24. Orbital implant 24 includes a plurality of through-holes 24, which in the example of FIGS. 7A and 7B are shown as four through-holes 24. Through-holes 24 diverge from an anterior direction to a posterior direction as the through-holes 24 pass through orbital implant 24.

A porous ceramic orbital implant characterised in that it comprises biocompatible strands passed a multiplicity of times through and between shafts within its body creating a muscle fixation platform on the anterior pole.

An implant according to claim 1 characterised in that the said muscle fixation platform provides sites for direct reattachment of the ocular muscles to the implant An implant according to claim 1 characterised in that the said shafts are placed equidistantly from each other and between 2 and 10 mm, but more preferably between 3 and 7 mm, even more preferably 4 to 6 mm, from the anterior point of the device An implant according to claim 1 characterised in that the outer surface is smooth allowing placement into the orbit, without creating problematic dragging on the orbital tissues or wound closure An implant according to claim 3 characterised in that the said shafts are arranged in a square pattern around the anterior point.

An implant according to claim 4 characterised in that the smooth surface is porous having a multitude of holes in excess of 20 microns but no greater than 1000 microns.

An implant according to any preceding claim characterised in that the smooth surface comprises additional windows cut through the smooth surface in areas where the strands comprising the muscle fixation platform lie allowing the attached muscles and soft tissue to directly contact the macroporous inner of the device.

An implant according to claim 7 characterised in that the smooth surface only extends partially onto the posterior hemisphere from the anterior hemisphere.

An implant according to any preceding claim characterised in that the area anteriorly to the muscle fixation platform is non-porous.

An implant according to any preceding claim characterised in that the macropores are spread between 50 and 1000 um but more preferably spread between 200 and 800 um An implant according to any preceding claim characterised in that the macropores of the body are fully interconnected An implant according to any preceding claim characterised in that the interconnections will be greater than 20 um but preferably greater than 50 um An implant according to any preceding claim characterised in that the ceramic particles are undersintered leaving microporosity between the ceramic particles.

An implant according to any preceding claim characterised in that the density of the said implant is between 0.2 grams per cubic centimeter and 0.8 grams per cubic centimeter Embodiments of the invention may further be understood or defined by reference to the following numbered paragraphs:

1) A porous ceramic orbital implant characterised in that it comprises biocompatible strands passed a multiplicity of times through and between shafts within its body creating a muscle fixation platform on the anterior pole.
2) An implant according to paragraph 1 characterised in that the said muscle fixation platform provides sites for direct reattachment of the ocular muscles to the implant
3) An implant according to paragraph 1 characterised in that the said shafts are placed equidistantly from each other and between 2 and 10 mm, but more preferably between 3 and 7 mm, even more preferably 4 to 6 mm, from the anterior point of the device
4) An implant according to paragraph 1 characterised in that the outer surface is smooth allowing placement into the orbit, without creating problematic dragging on the orbital tissues or wound closure
5) An implant according to paragraph 3 characterised in that the said shafts are arranged in a square pattern around the anterior point.
6) An implant according to paragraph 4 characterised in that the smooth surface is porous having a multitude of holes in excess of 20 microns but no greater than 1000 microns.
7) An implant according to any preceding numbered paragraph characterised in that the smooth surface comprises additional windows cut through the smooth surface in areas where the strands comprising the muscle fixation platform lie allowing the attached muscles and soft tissue to directly contact the macroporous inner of the device.
8) An implant according to paragraph 7 characterised in that the smooth surface only extends partially onto the posterior hemisphere from the anterior hemisphere.
9) An implant according to any preceding numbered paragraph characterised in that the area anteriorly to the muscle fixation platform is non-porous.
10) An implant according to any preceding numbered paragraph characterised in that the macropores are spread between 50 and 1000 um but more preferably spread between 200 and 800 um
11) An implant according to any preceding numbered paragraph characterised in that the macropores of the body are fully interconnected
12) An implant according to any preceding numbered paragraph characterised in that the interconnections will be greater than 20 um but preferably greater than 50 um
13) An implant according to any preceding numbered paragraph characterised in that the ceramic particles are undersintered leaving microporosity between the ceramic particles.
14) An implant according to any preceding numbered paragraph characterised in that the density of the said implant is between 0.2 grams per cubic centimeter and 0.8 grams per cubic centimeter Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. An orbital implant comprising a ceramic body including a plurality of through-holes incorporated into the ceramic body and at least one biocompatible thread threaded into the through-holes so as to provide a muscle attachment platform on an anterior side of the implant, the muscle attachment platform defined by at least one strand of the at least one biocompatible thread extending between at least two of the through-holes, wherein the muscle attachment platform is configured to provide a muscle attachment point on an external surface of the ceramic body for receiving a separate suture that sutures a muscle to the muscle attachment point of the muscle attachment platform.

2. An orbital implant as claimed in claim 1, wherein the at least one biocompatible thread is threaded between adjacent through-holes so as to provide the muscle attachment platform.

3. An implant as claimed in claim 2, wherein the at least one biocompatible thread is resorbable.

4. An implant as claimed in claim 1, wherein an outer surface of the implant is substantially smooth.

5. An implant as claimed in claim 1, wherein the ceramic body is porous.

6. An implant as claimed in claim 5, wherein the pores are fully interconnected.

7. An implant as claimed in claim 5, wherein the pores have diameters from 20 to 1000 μm.

8. An implant as claimed in claim 5, wherein the pores are spaced from each other on a surface of the implant by from 50 to 1000 μm.

9. An implant as claimed in claim 8, wherein the pores are spaced from each other on a surface of the implant by from 200 to 800 μm.

10. An implant as claimed in claim 5, wherein the ceramic body is macroporous.

11. An implant as claimed in claim 1, wherein portions of an outer surface of the implant are non-porous.

12. An implant as claimed in claim 11, wherein the non-porous portions of the surface are predominantly on an anterior side of the implant.

13. An implant as claimed in claim 11, wherein a surface of the implant at or near the muscle attachment platform is porous.

14. An implant as claimed in claim 1, wherein there are provided at least three through-holes.

15. An implant as claimed in claim 14, wherein the through-holes are arranged in a substantially regular polygonal configuration.

16. An implant as claimed in claim 15, wherein there are provided four through-holes.

17. An implant as claimed in claim 1, wherein the through-holes are located equidistantly from each other.

18. An implant as claimed in claim 1, wherein the through-holes are substantially parallel.

19. An implant as claimed in claim 1, wherein the through-holes one of converge and diverge from the anterior side of the implant to a posterior side of the implant.

20. An implant as claimed in claim 1, wherein the through-holes are located from 2 to 10 mm from an anterior point of the implant.

21. An implant as claimed in claim 20, wherein the through-holes are located from 3 to 7 mm from the anterior point of the implant.

22. An implant as claimed in claim 20, wherein the through-holes are located from 4 to 6 mm from the anterior point of the implant.

23. An implant as claimed in claim 1, wherein the through-holes have a diameter from 0.5 to 3 mm.

24. An implant as claimed in claim 1, having a density of 0.2 g/cm$^3$ to 0.8 g/cm$^3$.

25. An implant as claimed in claim 1, wherein the ceramic body is made of one of aluminium oxide and hydroxylapatite.

26. An implant as claimed in claim 1, wherein the ceramic body comprises ceramic particles that are undersintered leaving microporosity between the particles.

27. An orbital implant comprising a ceramic body including a plurality of through-holes incorporated into the ceramic body and at least one biocompatible thread threaded between adjacent through-holes so as to provide a muscle attachment platform on an anterior side of the implant, the muscle attachment platform defined by at least one strand of the at least one biocompatible thread extending between the adjacent through-holes, wherein the muscle attachment platform is configured to provide a muscle attachment point on an external surface of the ceramic body for receiving a separate suture that sutures a muscle to the muscle attachment point of the muscle attachment platform.

\* \* \* \* \*